(12) United States Patent
Visintin

(10) Patent No.: US 7,098,656 B2
(45) Date of Patent: Aug. 29, 2006

(54) MAGNETIC-INDUCTIVE DEVICE FOR THE CONTROL OF FERROMAGNETIC RETICLES

(75) Inventor: Roberto Visintin, Trieste (IT)

(73) Assignee: Security Control S.r.l., Sistiana (IT)

( * ) Notice: Subject to any disclaimer, the term of this patent is extended or adjusted under 35 U.S.C. 154(b) by 0 days.

(21) Appl. No.: 10/534,461

(22) PCT Filed: Dec. 18, 2002

(86) PCT No.: PCT/IT02/00804

§ 371 (c)(1),
(2), (4) Date: Sep. 8, 2005

(87) PCT Pub. No.: WO2004/055490

PCT Pub. Date: Jul. 1, 2004

(65) Prior Publication Data

US 2006/0119355 A1    Jun. 8, 2006

(51) Int. Cl.
G01B 7/30 (2006.01)
G01R 33/00 (2006.01)

(52) U.S. Cl. .................. 324/244; 324/207.25; 324/228

(58) Field of Classification Search ............ 324/207.25
See application file for complete search history.

(56) References Cited

U.S. PATENT DOCUMENTS 5,221,805 A    6/1993    Lace
5,901,534 A    5/1999    Weiss et al.
6,150,809 A    11/2000   Tiernan et al.
2001/0019263 A1 9/2001   Kwun et al.

FOREIGN PATENT DOCUMENTS

| EP | 0819944 | 1/1998 |
|---|---|---|
| GB | 526805 | 9/1940 |
| GB | 1270821 | 4/1972 |
| JP | 2002360537 | 12/2002 |

*Primary Examiner*—Bot LeDynh
(74) *Attorney, Agent, or Firm*—Dowell & Dowell, P.C.

(57) ABSTRACT

The device object of this patent is composed of:—one box (1) which is U-shaped in its transversal section;—two guiding plates (2) for the magnets (4);—two L-shaped rolled sections (3), which constitute the magnets (4) pole pieces;—various magnets (4) placed parallelly to the ferromagnetic insert (8) to be tested; each magnet (4) is placed parallel to the ferromagnetic insert (8) sliding direction with respect to the device and vice versa;—various measuring coils (5) placed in a housing (6), which is U-shaped in its transversal section;—a covering plate (7) fixed to box (1) in such a way to occupy the device side facing the insert (8) to be tested;—simple gears permitting to direct, in following times, the coils (5) parallelly to the different angles of the ferromagnetic insert (8) layers.

4 Claims, 4 Drawing Sheets

MAGNETIC-INDUCTIVE DEVICE FOR THE CONTROL OF FERROMAGNETIC RETICLES

TECHNICAL FIELD

This invention consists in a device that allows a non-destructive testing of the metal inserts made of ferromagnetic material in the form of wires and webs and is therefore particularly suitable for the inspection of tyres before being reconstructed.

BACKGROUND ART

The metal inserts in ferromagnetic material are used in different applications. They can be used as supporting elements of complex structures or as being part of particular single elements.

For example, the covering of a tyre has an internal insert of steel wires, which are criss-crossed to strenghten the whole structure.

Worn out tyres are covered with a new tread allowing in this way their recycling. The reconstructed tyre achieves, in this way, security levels which can be compared to a new tyre from any point of view. The application of stricts working procedures, from the acquisition and suitability testing of the structure, to very accurate pressure controls of the final product under working conditions, guarantees the high quality of the entire production process.

All wracks directed to reconstruction are in fact previously carefully examined through the utilization of suitable equipment, which verifies the conditions of suitability to reconstruction.

One of the main parameters taken into consideration is the integrity of the metal insert, which is usually tested through x-rays, ultrasounds equipments or through scirografy.

Unfortunately the non-destructive testing of ferromagnetic metal inserts using these appliances is rather expensive.

Two patents for non-destructive material tests are known, which make use of magnetism and electromagnetism. Patent US 2001/019263 describes an apparatus for testing the conditions of railroad rails. It consists in a wave generator/transmitter, inclusive of a solenoid, and in a wave receiver, also inclusive of a solenoid. Both have the same structure and each of them is enclosed.

This device includes a U-shaped box, representing the base and sides of the device itself. A guiding plate for the magnets develops orthogonal to the device along each end of the box. Each guiding plate is fixed to the two opposite sides. A L-shaped rolled section is in turn fixed to both the above mentioned guiding plates.

The box contains several magnets, the ends of which are held in the right position by the above mentioned guiding plates. Said rolled sections represent the magnet pole pieces. The box contains also several coils placed in a suitable shell. A covering plate is then fixed to the box, in order to occupy the side of the device facing the metallic insert to be examined. The measuring coils are positioned between the magnets and the metal insert, at the centre of the device. The box is equipped externally with at least a multiple signal power point. The box and the covering plate avoid the contact of the magnets and coils, respectively, with the operator's hands or with the object to be examined.

The inductor consists of pole pieces and permanent magnets made with long-lasting high-stability materials and placed on one or more planes parallel to the ferromagnetic metal insert to be examined. Each magnet is placed parallely to the sliding direction of the metal insert with respect to the device, object of this patent. When the device slides on the ferromagnetic metal insert, it is correct to say that each magnet is located parallely to the sliding direction of the device itself on the metal insert to be examined.

Each measuring coil is autonomously connected to the multiple signal power point. The coils can also have simple gears, which permit their rotation. It is therefore possible, later on, to direct them following the different angles of the metal layers with respect to the sliding axis of the object to be tested.

This device permits a non-destructive testing of the ferromagnetic insert, both on the surface and internal part of an object. The device creates a magnetic field, parallel to that of the insert itself. The position and the possible presence of a damage are identified by one or more coils that are placed in the magnetic field. The signals recorded by the coils are transmitted to a software obtaining a diagram which underlines the presence of defects (their position and extent).

BRIEF DESCRITION OF THE DRAWINGS

Further characteristics and advantages of this invention will become clearer with a description of some forms of execution of the device, preferred but not exclusive, which are illustrated indicatively, but not limited to, in the enclosed drawings.

MODE FOR CARRYING OUT THE INVENTION

Figure 1:
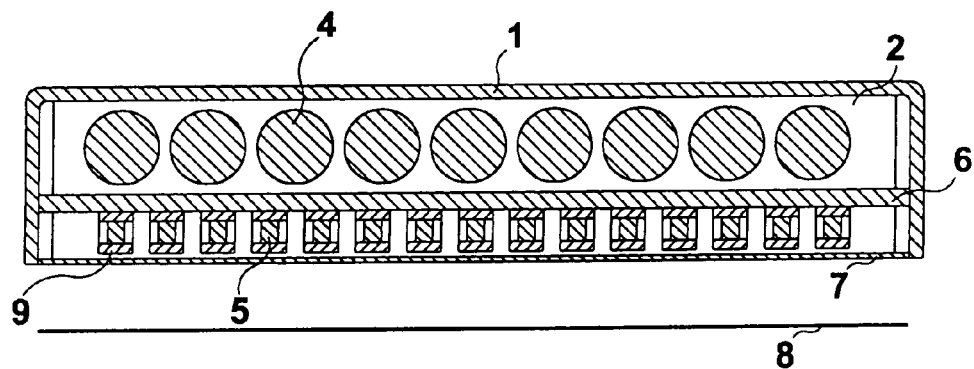
FIG. 1 shows a transversal section of a first device according to the invention.

More precisely the device on subject, in a first preferred embodiment shown in FIG. 1, is composed of an U-shaped box 1 in transversal section, constituting the device base and sides.

A guiding plate 2 for the magnets develops orthogonal to the device, along each end of box 1. Each guiding plate 2 is fixed to the opposite sides of box 1. Box 1 has externally at least one multiple signal power point and a stirrup for its fixing to the machinery. A L-shaped rolled section 3 is in turn fixed to each one of the above mentioned guiding plates 2.

Box 1 contains several magnets 4, the ends of which are held in the right position by holes made in the above mentioned guiding plates 2. Rolled sections 3 are magnets' 4 pole pieces.

Box 1 also contains several coils 5, located in a particular shell 6, which is U-shaped in its transversal section. A covering plate 7 is fixed to box 1 in order to occupy the device side facing the ferromagnetic insert 8 under examination. The coils 5 are placed between the magnets 4 and the metal insert 8, at the centre of the device.

Box 1 and covering plate 7 avoid contacts of magnets 4 and coils 5, respectively, with the operator's hands and the object containing the ferromagnetic insert 8. The inductor is composed of the polar pieces and the permanent magnets 4 made with long-lasting high-stability materials and placed on one or more parallel planes to the ferromagnetic insert 8 to be tested. Each magnet 4 is placed parallel to the sliding direction of the insert 8 with respect to the device object of this patent. When the device slides on the insert 8, it is possible to say that each magnet 4 is placed parallel to the sliding direction of the device on the ferromagnetic insert 8 to be tested.

Figure 2:
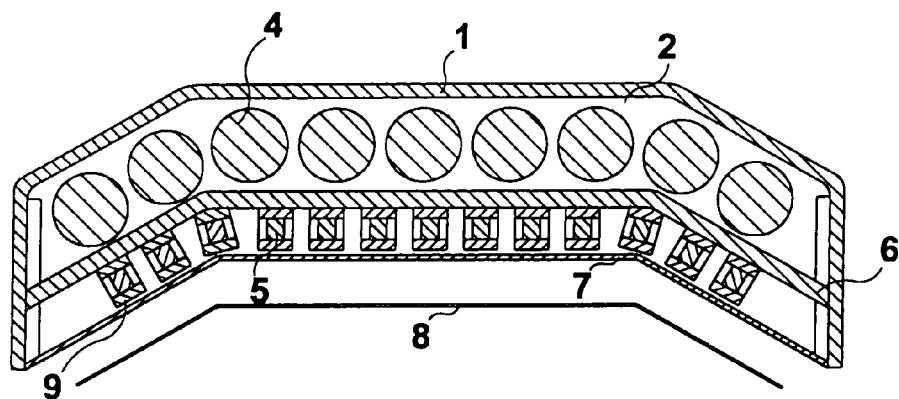
FIG. 2 shows a transversal section of a second device according to the invention.
Figure 3:
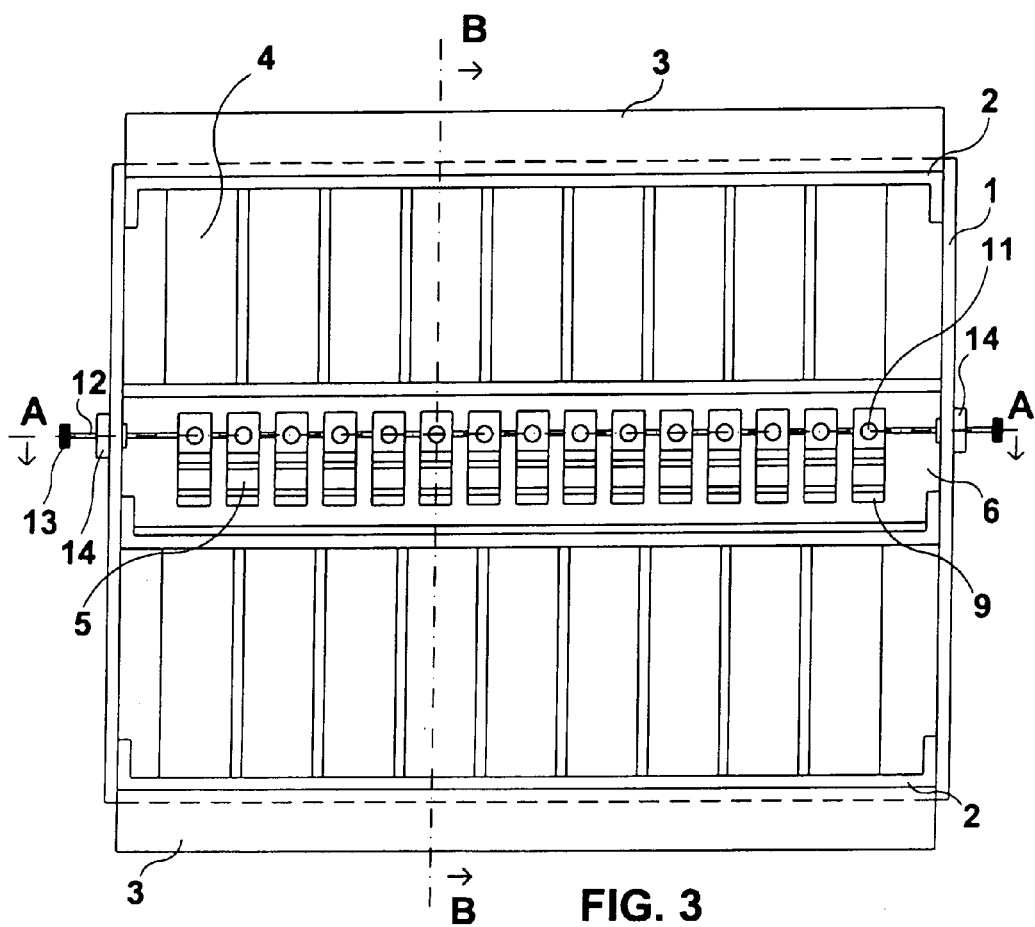
FIG. 3 shows a frontal view of a third device according to the invention without covering plate.
Figure 4:
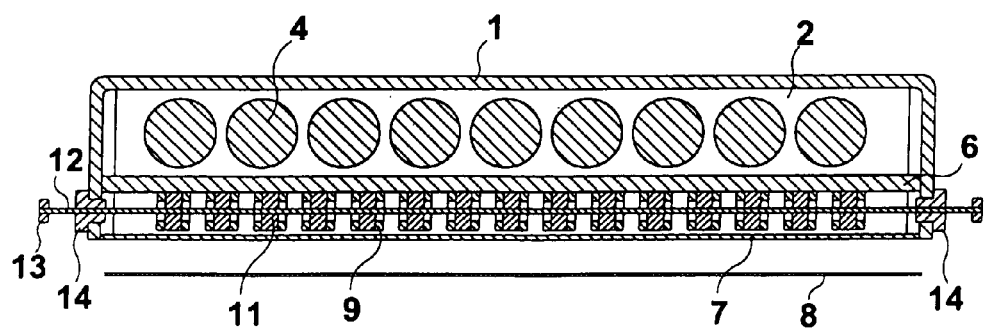
FIG. 4 shows a transversal section of the device at FIG. 3, along the plane A—A.
Figure 5:
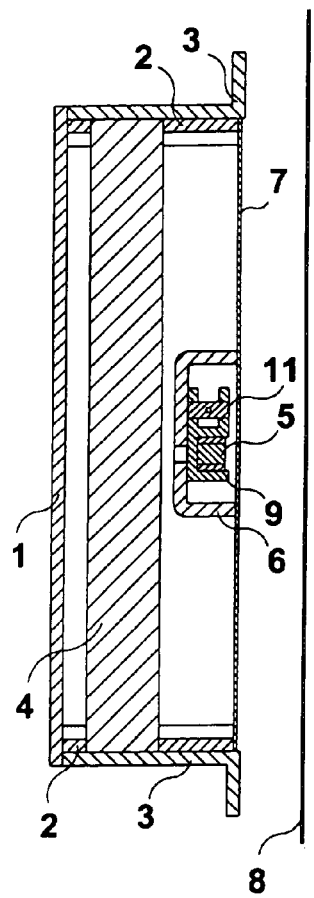
FIG. 5 shows a transversal section of the device at FIG. 3, along the plane B—B.
Figure 8:
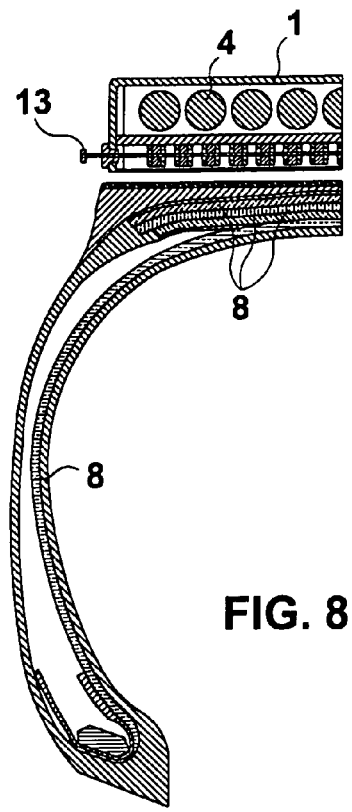
FIG. 8 shows a partial view of the device during a tyre testing.
Figure 6:
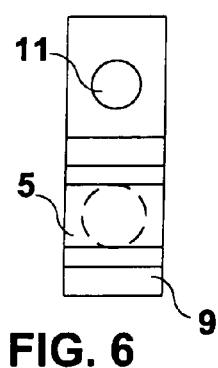
FIG. 6 shows an enlarged frontal view of the coil and turning stand of the device at FIG. 3.
Figure 7:
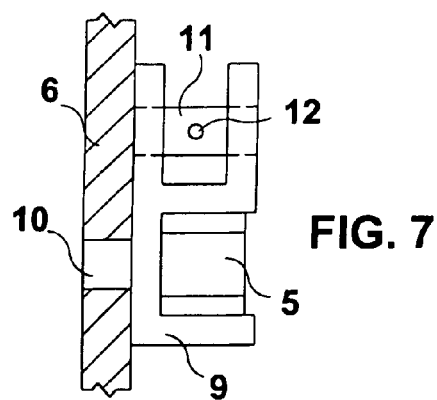
FIG. 7 shows an enlarged longitudinal view of the same coil and turning stand.
Figure 9:
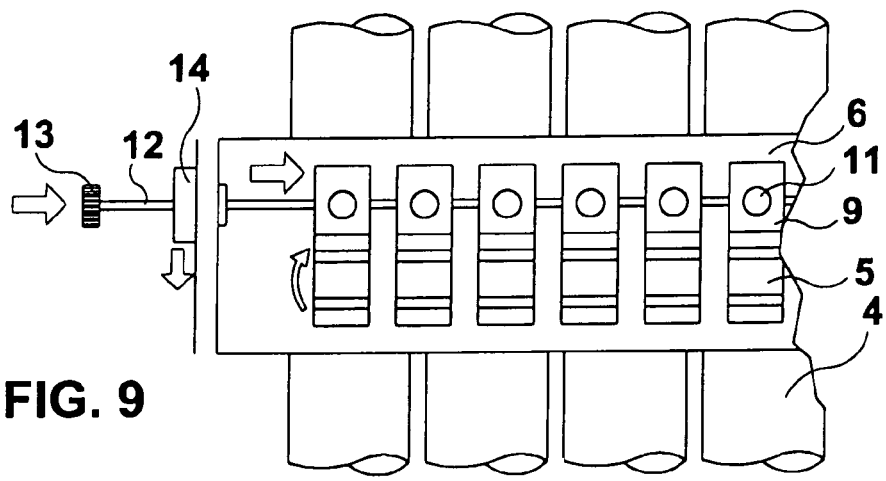
FIGS. 9 and 10 show other partial enlarged frontal views of the device at FIG. 3 with a different positioning of the measuring coils.
Figure 10:
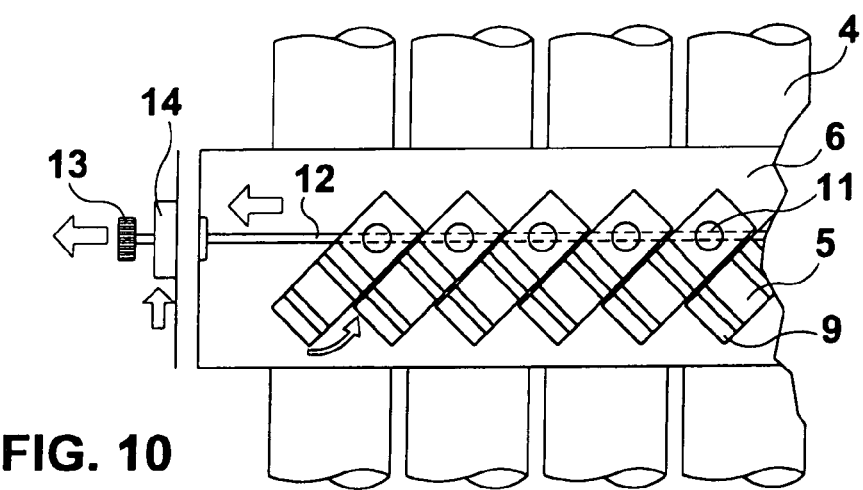

Each coil 5 is autonomously connected to the multiple signal power point. The device object of this patent can have a transversal fitted shape permitting to test inserts 8 having different shaped planes. The device on subject, in a second preferred embodiment shown in FIG. 2, shows for example a transversal shape with a central plane and two inclined sides. The permanent magnets 4 are placed on three planes, each of them parallel to one plane of the metal ferromagnetic insert 8 to be examined. Coils 5 can be equipped with simple gears permitting their rotation.

In the device on subject, in a third preferred embodiment shown from FIG. 3 to FIG. 10, each coil 5 is inserted in its stand 9. This stand has a pin 10 and a screwed roller 11. Each screwed roller 11 is crossed by a screwed bar 12. This bar has on both ends a knob 13 and a bushing 14 sliding along the device side. The screwed bar 12 crosses transversally the entire device. Pins 10 are stuck in particular holes made in the housing base 6 on which the coils 5 are placed. Pushing with a knob 13 the screwed bar towards the device internal part forces all screwed rollers 11 to move in one direction letting rotate the different housings 9, which have pins 10 as their fulcrum. In this way it is possible to direct the coils 5 parallely to one of the angles along which are placed the metal layers of the ferromagnetic insert 8. When pulling the knob 13 towards the device external part, the coils 5 are forced to align parallely to another angle of the metal layer of the insert 8.

Therefore the ferromagnetic insert 8 can be tested in following moments along all directions in which the metal layers composing the insert itself are directed.

Figure 11:
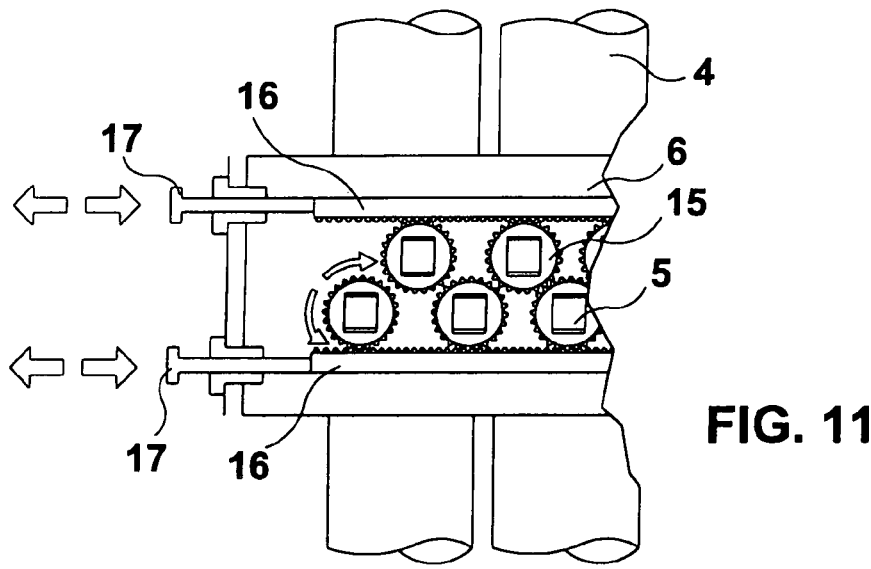
FIG. 11 shows a partial enlarged frontal view of a device which has different possibilities of coil positioning.

In the device on subject, in a fourth preferred embodiment shown in FIG. 11 each coil 5 has its own toothed rotating stand 15. This stand has a pin stuck in a hole made in the housing base 6 on which are placed the coils 5. A rack 16 or worm screw crosses the device transversally.

By moving a knob 17, placed at the rack end or at the worm screw end, the toothed turning stands 15 rotate and fit into the rack 16 or into the worm screw itself. In this case too it is possible to test the insert 8 along multiple directions.

The invention claimed is:

1. Magnetic-inductive device for the control of ferromagnetic reticles, composed of a U-shaped box (1) in transversal section, which is the base and sides of the device itself, several magnets (4) made with long-lasting high-stability materials, several measuring coils (5), at least one multiple signal power point placed externally to the box (1) and one stirrup for its fixing to the device; said device is characterized by the fact of moreover comprising:

at least two guiding plates (2) for the magnets (4); each of said at least two guiding plates (2) develops orthogonally to the device along each box (1) end and is fixed to the opposite two sides of the box (1) itself;

two L-shaped rolled sections (3), each developping orthogonally to the device along each box (1) end and both fixed to one of said at least two guiding plates (2); said rolled sections (3) constitute the magnets pole pieces (4);

several said magnets (4), the ends of which are held in the right position by holes made in said at least two guiding plates (2); the inductor is composed of the polar pieces and the permanent magnets (4), which are placed on one or more parallel planes of a ferromagnetic insert to be tested; each magnet (4) is placed parallel to the ferromagnetic insert (8) sliding direction with respect to the device itself; vice versa, when the device is to slide on the insert (8), it is possible to confirm that each magnet (4) is placed parallel to the device sliding direction on the insert (8);

several coils (5) placed in a housing (6) which is U-shaped in its transversal section; said coils (5) are placed between the magnets (4) and the ferromagnetic insert (8) at the centre of the device; each coil (5) is autonomously connected to said multiple signal power point; the signals recorded by the measuring coils (5) are transmitted to a software, producing a diagram that underlines the position and the extent of any damage found in the ferromagnetic insert (8);

a covering plate (7) fixed to box (1) so that it occupies the device side facing the ferromagnetic insert (8) to be examined;

simple gears which enable the coils (5) to rotate parallel, in following times, along all directions in which the insert (8) metal layers are directed.

2. Magnetic-inductive device, according to claim 1, characterized by the fact of having a transversal shape suitable to test ferromagnetic inserts (8) shaped along different planes; said permanent magnets (4) are placed on different planes, each one being parallel to a plane of the insert (8) to be examined.

3. Magnetic-inductive device, according to claim 1, characterized by the fact that said gears, enabling the coils (5) to turn, consist of stands (9), each one housing a coil (5); each of said strands (9) has a pin (10) and a screwed roller (11); each screwed roller (11) is crossed by a screwed bar (12) having on at least one of its ends a knob (13) and a bushing (14), which slides along the device side; said screwed bar (12) crosses the device transversally; the above referenced pins (10) are stuck in particular holes made in the housing (6) where the coils (5) are placed; by pushing with this knob (13) the connected screwed bar (12) in one direction or in the other, all screwed rollers (11) are forced to move and they make turn the different stands (9), which have the pins (10) as fulcrum.

4. Magnetic-inductive device, according to claim 1, characterized by the fact that said gears, enabling the coils (5) to turn, are composed of toothed turning stands (15), each one housing a coil (5); each stand (15) has got a pin stuck in a hole drilled in the housing (6) on which the coils (5) are placed; a rack (16) or a worm screw crosses transversally the device; by pushing in one direction or in the other a knob (17) connected to a rack (16) or a worm screw, all toothed turning stands (15) are forced to rotate on their own pins.

\* \* \* \* \*